(12) United States Patent
Amara et al.

(10) Patent No.: US 8,298,146 B2
(45) Date of Patent: Oct. 30, 2012

(54) CIRCULAR ULTRASOUND TOMOGRAPHY SCANNER AND METHOD

(75) Inventors: Arie Amara, Misgav (IL); Avi Amara, Menashe (IL)

(73) Assignee: Helix Medical Systems Ltd., Kiryat-Shmona (IL)

( * ) Notice: Subject to any disclaimer, the term of this patent is extended or adjusted under 35 U.S.C. 154(b) by 1745 days.

(21) Appl. No.: 10/559,078

(22) PCT Filed: Mar. 15, 2005

(86) PCT No.: PCT/IL2005/000290
§ 371 (c)(1),
(2), (4) Date: Dec. 2, 2005

(87) PCT Pub. No.: WO2005/087110
PCT Pub. Date: Sep. 22, 2005

(65) Prior Publication Data
US 2006/0173307 A1 Aug. 3, 2006

Related U.S. Application Data

(60) Provisional application No. 60/553,134, filed on Mar. 16, 2004.

(51) Int. Cl.
*A61B 8/00* (2006.01)
(52) U.S. Cl. ........ 600/443; 600/407; 600/445; 600/437; 600/446
(58) Field of Classification Search ................ 600/407, 600/445, 437, 443
See application file for complete search history.

(56) References Cited

U.S. PATENT DOCUMENTS

| | | | |
|---|---|---|---|
| 4,130,112 A | 12/1978 | Frazer | |
| 4,206,763 A * | 6/1980 | Pedersen | 600/445 |
| 4,545,385 A | 10/1985 | Pirschel | |
| 5,664,573 A * | 9/1997 | Shmulewitz | 600/445 |
| 6,304,770 B1 | 10/2001 | Lee et al. | |
| 6,377,838 B1 * | 4/2002 | Iwanczyk et al. | 600/425 |
| 2,323,311 A1 | 12/2003 | Jesseph | |
| 7,166,075 B2 * | 1/2007 | Varghese et al. | 600/439 |
| 2003/0233110 A1 | 12/2003 | Jesseph | |

FOREIGN PATENT DOCUMENTS

DE 32 24 290 A1 12/1983
(Continued)

OTHER PUBLICATIONS

Communication Pursuant to Article 94(3) EPC Dated Oct. 1, 2009 From the European Patent Office Re.: Application No. 05718863.3.
International Preliminary Report on Patentability Dated Oct. 2, 2006 From the International Bureau of WIPO Re.: Application No. PCT/IL2005/000290.

(Continued)

*Primary Examiner* — Brian Casler
*Assistant Examiner* — Joel Lamprecht

(57) ABSTRACT

A portable mechanical high-precision device for performing circular or helical scanning of a patient's organ or body surface for tissue diagnosis and/or treatment includes a substantially hollow housing for accommodating the organ therein and a securing unit for securing the housing to the organ or body surface during scanning so that the organ or body surface is substantially fixed relative to the housing. At least one drive unit is attached to the housing and to at least one scan head for allowing unlimited rotation of the scan head relative to the housing.

45 Claims, 10 Drawing Sheets

FOREIGN PATENT DOCUMENTS

| | | |
|---|---|---|
| DE | 3224290 | 12/1983 |
| DE | 03224290 | 12/1983 |
| WO | WO 03/103500 | 12/2003 |
| WO | WO 03/103500 A1 | 12/2003 |
| WO | WO 03103500 A1 * | 12/2003 |
| WO | WO 2005/087110 | 9/2005 |

OTHER PUBLICATIONS

International Search Report and the Written Opinion Dated Sep. 22, 2005 From the International Searching Authority Re.: Application No. PCT/IL2005/000290.

* cited by examiner

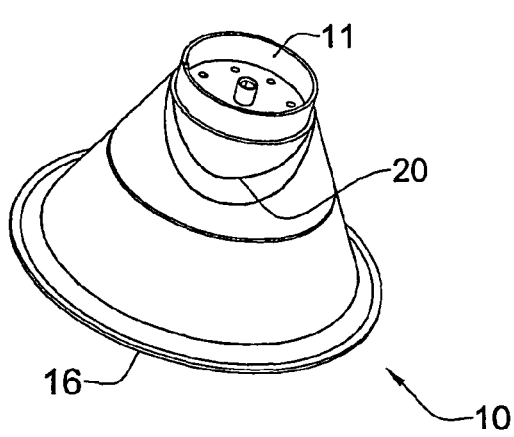 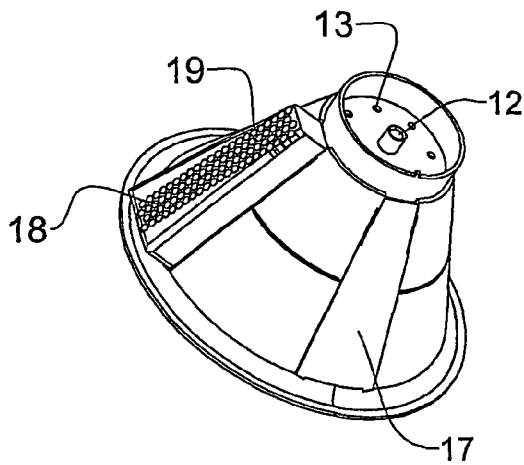
FIG. 1A    FIG. 1B
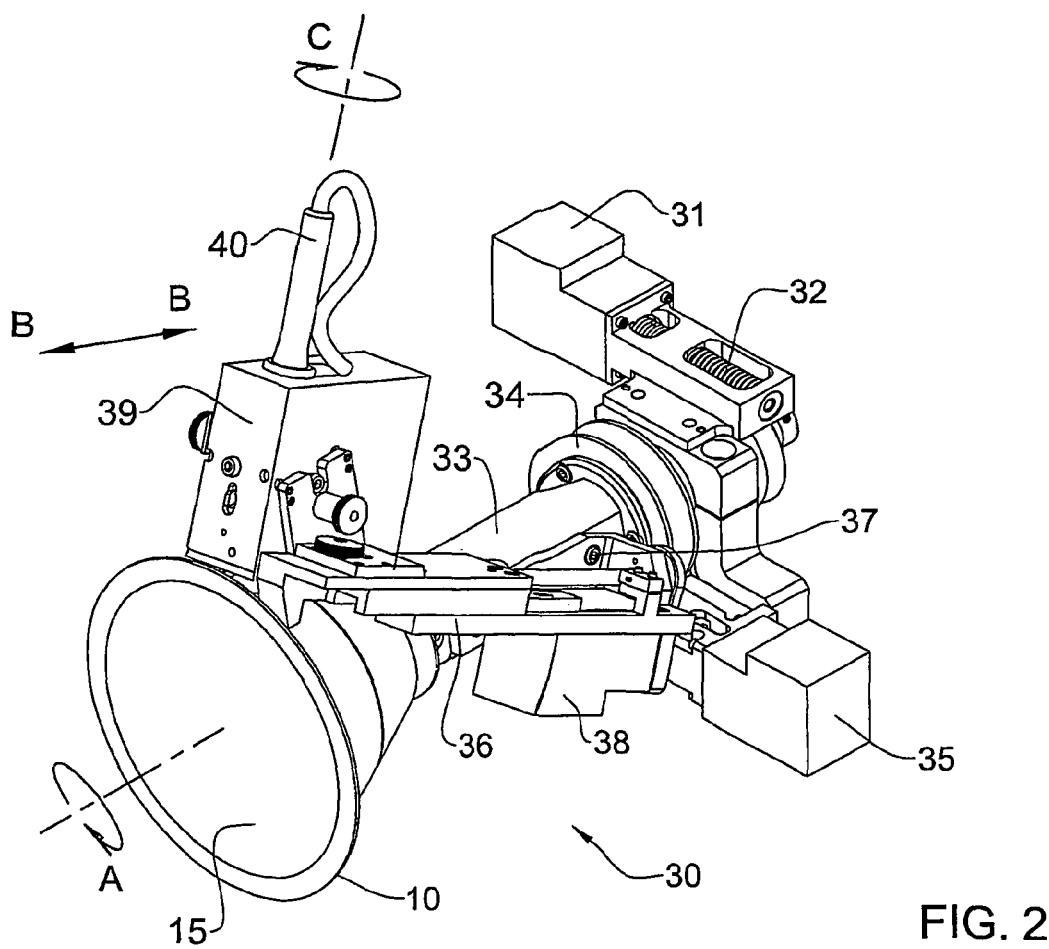
FIG. 2

$Im(x,y,z) = \sum Im(r,w,\theta,\alpha)$

CIRCULAR ULTRASOUND TOMOGRAPHY SCANNER AND METHOD

FIELD OF THE INVENTION

This invention relates to ultrasound tomography particularly, albeit not exclusively, for diagnosis and treatment of breast tumors.

BACKGROUND OF THE INVENTION

It is known to obtain ultrasound images of the breast using a probe placed against the breast. Stereotactic biopsy techniques are done in a similar fashion; with a patient lying prone, with the breast hanging through a hole in the table. All these methods have shortcomings related to the flaccid nature of the breast which leads to difficulty in manipulating and orienting the organ. Additionally, some of these methods are very uncomfortable for the patient, the pain often associated with the forceful compression of the breast between plates in mammography being a prime example.

US 2003/0233110A1 (Jesseph) published Dec. 18, 2003 and entitled "Device and method for improved diagnosis and treatment of cancer" discloses a fixation device, which fixes a breast in distended, stable position using negative pressure, and minimizes or halts lymphatic flow from the breast. An image-guided system allows accurate and bloodless access to breast tissue guided by MRI or CT. Linear and rotary configurations are disclosed. The device employs a cup-like chamber that surrounds the breast and has top and bottom ends that are both open as well as a fluid evacuation duct for allowing the chamber to be secured to the breast by applying suction to the top end. Application of suction causes the breast to elongate and fill the internal volume of the chamber, whereupon it may be placed in an imaging or interventional device such as an MRI coil, ultrasound device, CT scanner, and the like.

It is clear that the imaging or interventional device is a separate unit from the fixation device, which serves only to contain and hold the breast in optimum position for subsequent scanning by a discrete scanning unit.

WO03103500A1 (Duck et al.) published Dec. 18, 2003 and entitled "Ultrasonic imaging device" discloses a device for use in the imaging of breast tissue comprising a mounting structure capable of holding an ultrasound transducer having an effective transmission face and a tissue moulding element for receiving and surrounding the breast tissue. The mounting structure is movable relative to the surface of the breast tissue placed into the tissue moulding element, so that on rotation of the mounting structure, the ultrasound transducer attached thereto encircles the breast substantially parallel to a surface of the breast.

In such an arrangement the scan head typically rotates together with the housing. Consequently, during use there is a tendency for the breast to move together with the rotating housing. Such movement is minimized by introducing oil between the breast and the inner surface of the housing, but even slight tendency for the breast to rotate causes inaccuracies in the scanned image.

Moreover, the fact that the housing moves relative to the breast militates against securing the breast within the housing. It is stated that the tissue moulding element may be stationary relative to the breast. It is also stated that negative pressure may be applied to the tissue moulding element so as to enhance the moulding of the breast placed therein. However, there appears to be no teaching in WO03103500A1 as to how the breast may be fixed within the tissue moulding element such that the mounting structure may move unimpeded around the tissue moulding element. To the contrary, the sole figure in WO03103500A1 shows a recess or window within the tissue moulding element that accommodates the ultrasonic transducer, such that the ultrasonic transducer is constrained to rotate with the tissue moulding element. Moreover, a single motor is shown that rotates the two together, there being no provision to rotate the ultrasonic transducer independent of the tissue moulding element. Additionally, the tissue moulding element is shown as a conical housing that is supported on one side by a bracket fixed to the same support surface to which the motor is rotatably coupled and which has on an opposite side the recess or window for accommodating the ultrasonic transducer. It thus emerges that even if the recess or window were absent and the ultrasonic transducer were capable of rotation independent of the tissue moulding element, the bracket would get in the way of the ultrasonic transducer thus preventing unimpeded rotation thereof.

SUMMARY OF THE INVENTION

It is therefore an object of the invention to provide a portable mechanical high-precision device for performing unlimited circular or helical or linear scanning of a patient's organ or body surface.

To this end, there is provided in accordance with a first aspect of the invention a portable mechanical high-precision device for performing circular or helical scanning of a patient's organ for tissue diagnosis and/or treatment, a substantially hollow housing having an opening at a first end thereof for accommodating therein said organ or body surface proximate to said organ, a securing unit for securing the housing to the organ or body surface during scanning thereof so that the organ or body surface is substantially fixed relative to the housing, at least one scan head, and at least one drive unit attached to the housing and to the at least one scan head for allowing unlimited rotation of the scan head relative to the housing.

In accordance with a second aspect, the scan head is an ultrasonic device and there is provided a method for use thereof including:

moving the scan head relative to the patient's organ while emitting ultrasound at a first frequency;

receiving at a receiver of the scan head successive ultrasound signals each having respective second frequencies;

for each location of the scan head determining a Doppler shift between the first frequency and the respective second frequency; and using the respective Doppler shift at each location of the scan head to compute tissue movement or blood flow.

In accordance with a third aspect of the invention, there is provided a method for performing diagnosis of suspected tissue using a device according to the invention wherein a region of a surface of the housing is provided with at least one self-sealable aperture to enable penetration of a diagnosis or treatment tool therethrough, said region having a length substantially equal to an axial length of the housing or a projection of said axial length on said surface, said method comprising:

determining an initial location of the suspected tissue relative to the scan head of the device;

affixing said device so that said area overlaps said initial location;

partially scanning the patient's organ so as to identify at least a portion of the suspected tissue and determine at least partial coordinates thereof;

correlating the at least partial coordinates of said portion with the initial location of the suspected tissue so as to determine an offset of an origin of said area relative to the scan head;

computing which of said holes is aligned with the suspect tissue; and introducing the biopsy tool through said hole.

The invention also provides in another aspect a system for computing and displaying tissue movement or blood flow of an organ, the system comprising:

an ECG Monitor having LA, RA and LL leads for attaching to a patient for monitoring the patient's heart, a display coupled to the ECG Monitor for displaying an ECG of the patient's heart and determining the quiet cardiac phase, a multi-channel and multi-gate Trans-Cranial Doppler (TCD) system for detecting blood flow through said organ, and a custom scan head having two or more TCD probes with fixed known angles configured for mounting on the patient's organ.

BRIEF DESCRIPTION OF THE DRAWINGS

In order to understand the invention and to see how it may be carried out in practice, a preferred embodiment will now be described with regard to a device for ultrasound scanning of a breast, by way of non-limiting example only, and with reference to the accompanying drawings, in which:

FIGS. 1a and 1b are pictorial representations showing a housing according to an exemplary embodiment of the invention for accommodating a breast during scanning;

FIGS. 2 to 4 are pictorial representations showing the principal components in a device for scanning a patient's breast tissue according to an exemplary embodiment of the invention;

DETAILED DESCRIPTION OF EXEMPLARY EMBODIMENTS

Figure 3:
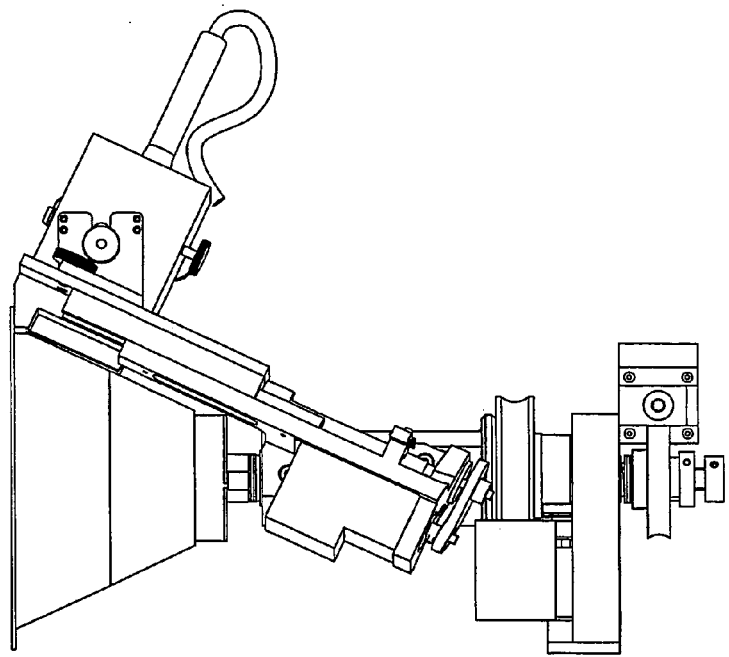

In the following description, components having similar functionality in more than one figure will be referenced in all figures by identical reference numerals.

FIGS. 1a and 1b show pictorially a substantially conical housing 10 according to an exemplary embodiment of the invention for accommodating a breast (not shown) during scanning. The housing 10, which may be disposable, has a first end 11 having a threaded portion 12 for threadably attaching to a motor unit so as to allow rotation of the housing. Apertures 13 formed in the first end 11 of the housing cooperate with a vacuum pump (not shown) for allowing suction to be applied. The apertures 13 thus operate as a securing unit for securing the breast within the housing and thereby avoid dislocation thereof during scanning, which if not prevented would derogate from the accuracy of subsequent measurements. A second end 15 of the housing is open to allow for insertion of the breast and is provided with a circumferential flange 16 for adding strength and rigidity. Although the surface of the housing is shown as conical it can be polyhedral and/or may be provided with one or more planar wall sections 17 that facilitate linear scanning along a section of the housing as will be explained in more detail below.

In accordance with an embodiment of the invention, a region 18 of a surface of the housing 10 is provided with at least one self-sealable aperture 19, which serves as a window for inserting a diagnosis or treatment tool therethrough. The self-sealable apertures 19 may either be lined with an elastomeric material that allows penetration of the tool and self-seals when the tool is withdrawn or may be covered with a removable, sealed layer that may be peeled off after applying suction to the housing. In order to ensure accurate insertion of such a tool so as to penetrate a volume of breast tissue that has been found to be suspect, two distinct approaches are feasible. In one approach as shown in FIG. 1b, the region 18 supports a matrix of self-sealable apertures 19 allowing manual insertion of the tool through a specific aperture (constituting a guide aperture) that ensures proper alignment with the volume of suspect tissue. Alternatively, the tool may be guided by a penetration robot having sufficiently fine resolution, in which case the holes may be dispensed with and an open self-sealable elastomer window may be provided. Thus, the aperture 19 can be a complete window or a matrix of multiple bores. In either case, a wall thickness of the region 18 is sufficient and optionally greater than a wall thickness of a remainder of the housing to serve as a guide for the diagnosis or treatment tool. In the case of PET, SPECT etc. the whole housing 10 can be thick; but for ultrasound, the wall thickness must be thin and in this case the region 18 containing the holes may project a couple of millimeters out of the housing as shown in FIG. 1b. If desired, the housing may be formed of mutually rotatable inner and outer wall portions, with a matrix of apertures formed on the inner wall portion and a window formed on the outer wall portion, thus allowing the window to be rotated into registration with the apertures.

The region 18 is dimensioned to extend along the complete axial length of the housing or a projection of the axial length on the surface of the housing so as to allow simultaneous access to all parts of the tissue contained along the axial length of the housing. As a result, the window defined by the region 18 may be rotated to a required location so as to allow complete access to a volume of breast tissue containing a suspect tumor or other artifact.

Part of the outer surface of the housing 10 shown in FIG. 1a is cut away to reveal that an top inside surface of the housing is formed with a inwardly depending solid protuberance 20 that prevents the nipple from reaching the end of the housing and defines an area that is not irradiated.

Figure 4:
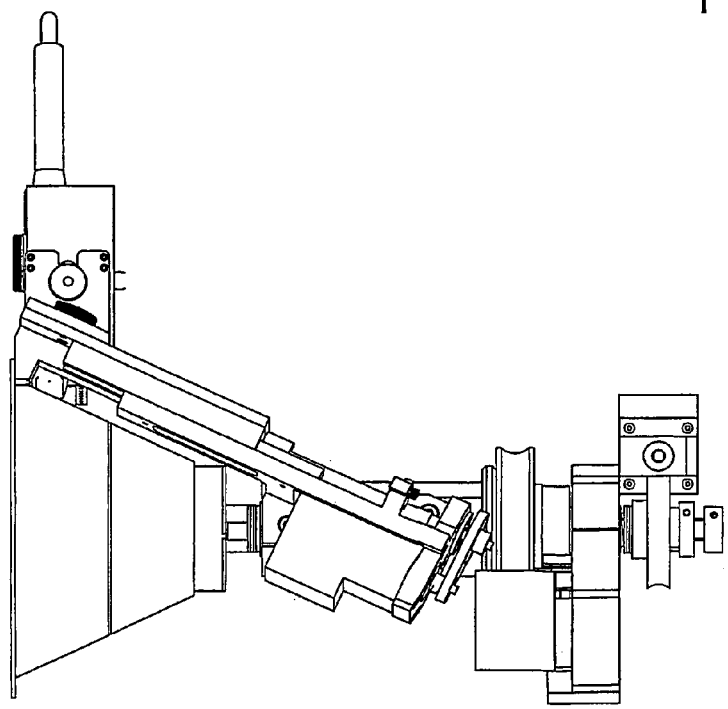

Having described the housing 10 in detail, there will now be described with reference to FIGS. 2, to 4 principal components in a device 30 for scanning a patient's breast tissue using the housing 10. Although the preferred embodiment is described with particular reference to the scanning of breast tissue, it is to be understood that the principles of the invention are equally applicable to other body tissues, provided that suitable adjustments are made to the design of the housing.

For example, the housing may be shaped internally to accommodate a limb such as a hand or foot, or a surface of body tissue such as liver, kidney or heart, thereby allowing scanning and subsequent biopsy or treatment thereof.

The device 30 comprises a first motor 31 adapted to rotate the housing 10 via a worm gear drive 32. To this end, the threaded portion 12 in the first end 11 of the housing 10 is connected via a complementary threaded portion (not shown) to one end of a coupler unit (concealed in the figure) whose other end is coupled to the worm gear drive 32. The coupler unit is surrounded by an outer sleeve 33 that is free to rotate relative to the housing 10 and is provided at an end remote from the housing with a peripheral coupling 34 that is rotatably coupled to a second motor 35. A bracket assembly 36 is fixed to the sleeve 33 via a pair of bolts such as 37 and supports a linear motor 38 (constituting a third motor) that is articulatedly coupled to a scan head assembly 39 accommodating therein an ultrasound probe 40. In such an arrangement, the first motor 31 is adapted to rotate the housing 10 only about an axis A, while the second motor 35 is adapted to rotate the scan head assembly 39 together with the linear motor 38 relative to the housing 10 also about the axis A. Either during such rotation of the scan head assembly 39 or independent thereof, the scan head assembly may be moved linearly up and down the outer wall of the housing 10 in the direction of B-B along a line parallel to an axis thereof. By such means, the scan head assembly is amenable to three types of motion: circular motion by driving the second motor 35 only; linear motion by driving the linear motor 38 only; and helical motion by driving both motors 35 and 38 simultaneously. Additionally, the scan head can be rotated manually between two mutually orthogonal positions as shown in FIGS. 3 and 4. In the first position shown in FIGS. 2 and 3, the scan head is adapted for rotary scanning about axis A around the surface of the housing. In the second position shown in FIG. 4, the scan head is rotated through 90° about an axis C normal to an active surface of the scan head so as to be adapted for linear scanning in the direction of B-B along the surface of the housing. During use, the first end 11 of the housing is coupled to a vacuum pump (not shown) for applying suction via the apertures 13.

Figure 5:
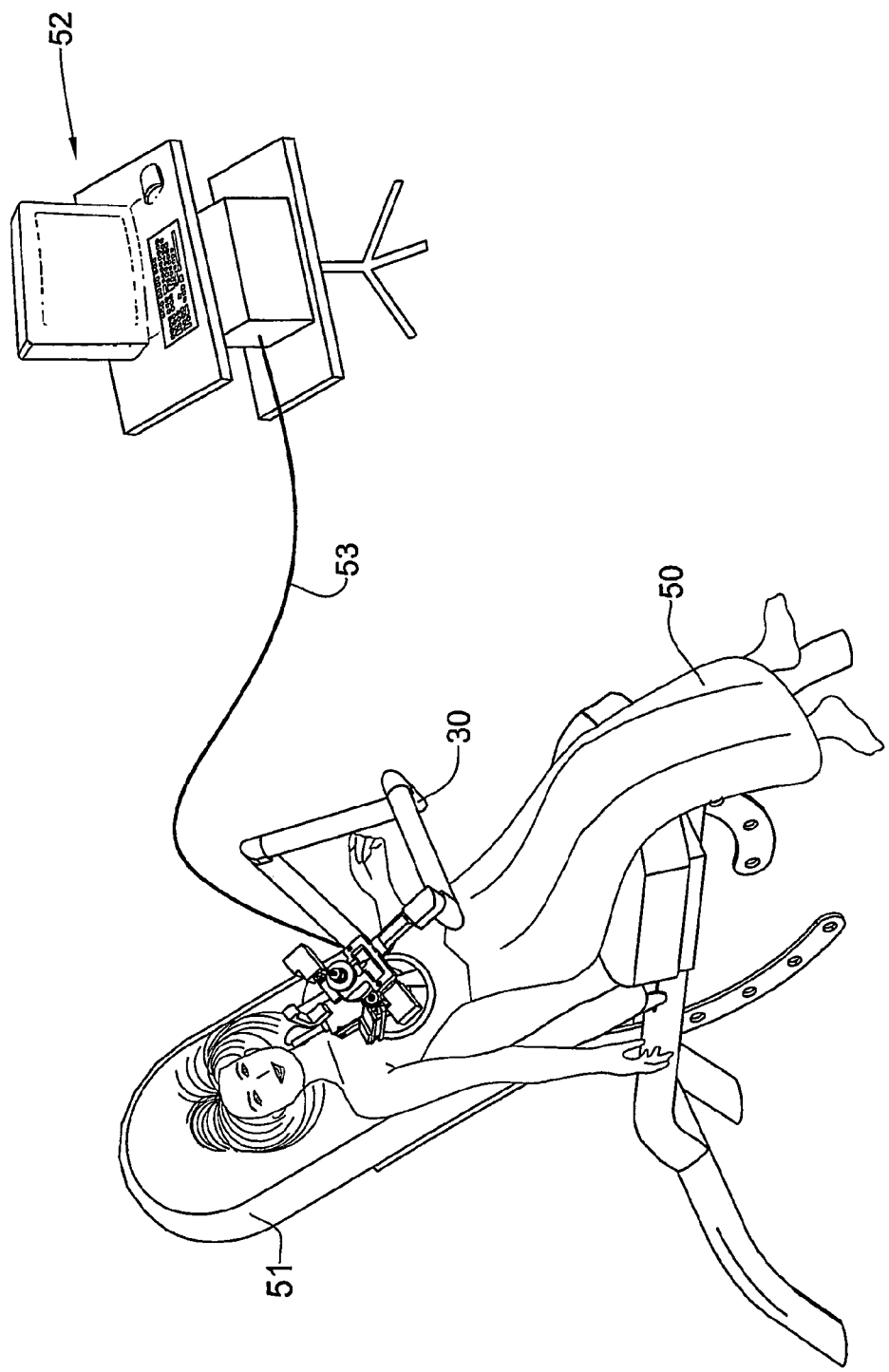
FIGS. 5 and 6 are pictorial representations showing use of the device for diagnosis and treatment of a breast tissue.
Figure 6:
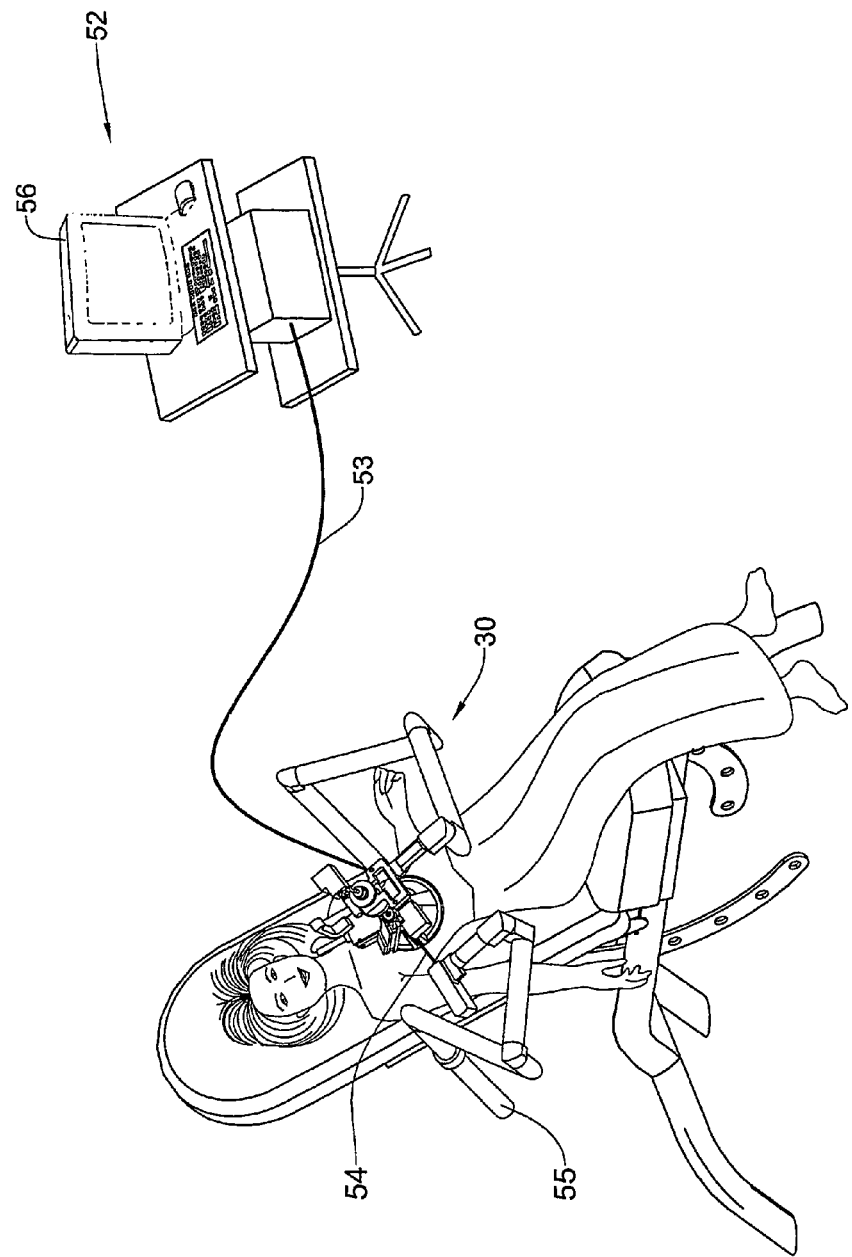
Figure 7:
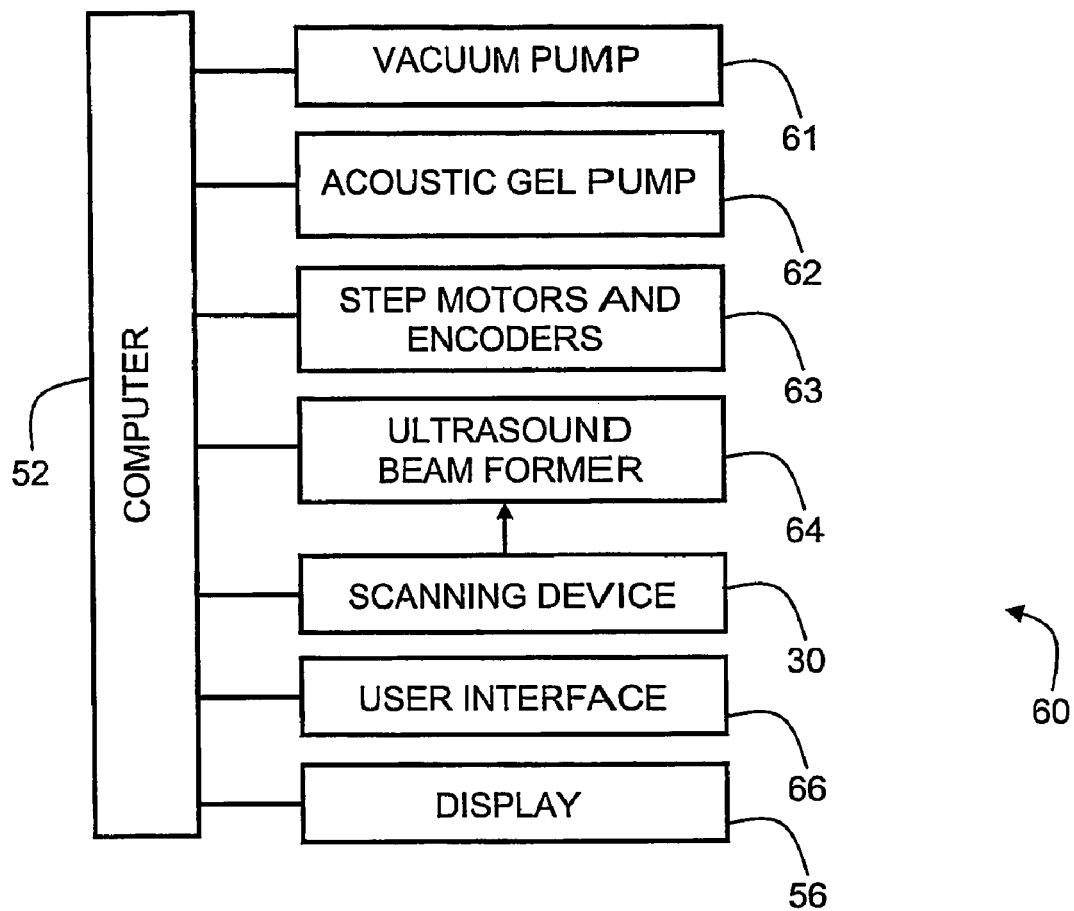
FIG. 7 is a block diagram showing the functionality of a system employing the device illustrated in FIGS. 5 and 6.
Figure 8:
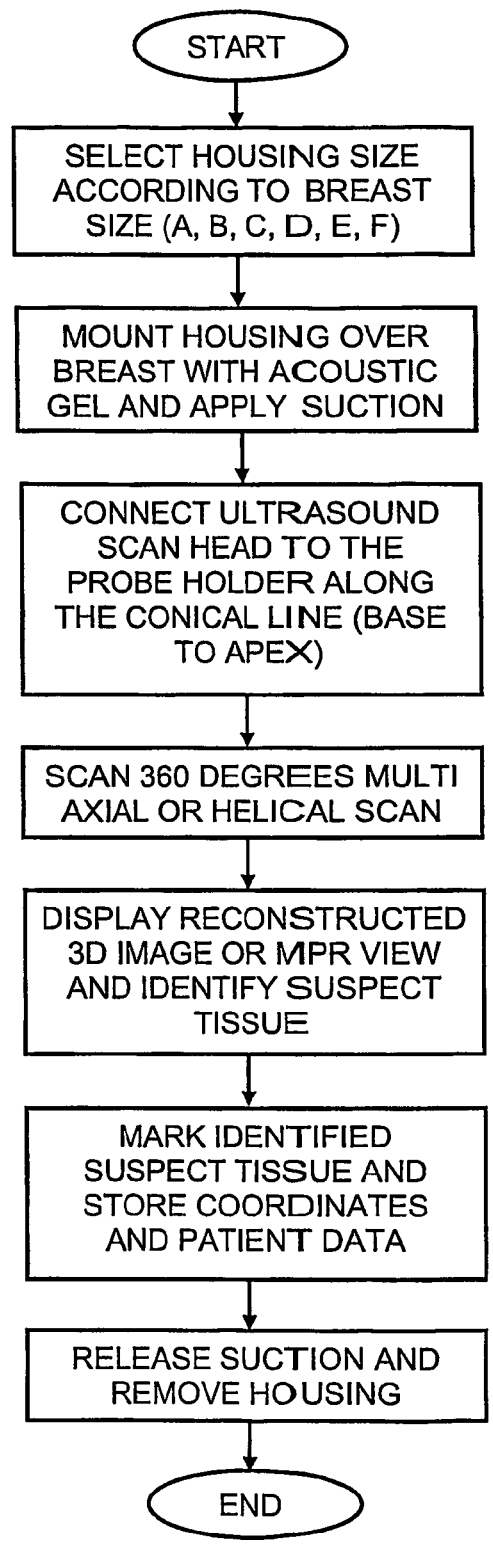
FIGS. 8 and 9 are flow diagrams showing the principal operations carried out by methods for using the device for initial scanning and subsequent diagnosis and/or treatment of a breast tissue.

FIGS. 5 and 6 are pictorial representations showing use of the device 30 for diagnosis and treatment of a breast tissue. A patient 50 is seated in a suitable support 51, such as a chair or reclining bed, and a housing of suitable size is coupled to the device 30 for mounting over one of the patient's breasts. Two distinct modes of operation of the device are possible as will now be described with reference to the flow diagrams of FIGS. 7 and 8 showing the principal operations carried out by methods for using the device for initial scanning and subsequent diagnosis and/or treatment of a breast tissue. These two modes are shown pictorially in FIGS. 5 and 6, respectively. Scanning always precedes diagnosis or treatment, either directly beforehand or more typically during a previous visit, where the patient's breasts are scanned and data is stored in a computer 52 coupled to the device 30 by a cable 53.

FIG. 7 is a block diagram showing the functionality of a system 60 employing the scanning device 30 and the computer 52 and display 56 illustrated in FIGS. 5 and 6. The computer 52 is coupled to a vacuum pump 61 and an acoustic gel pump 62 for controlling the application and release of suction and injecting the acoustic gel via suitable orifices at the end of the housing. The computer 52 is likewise coupled to stepper motors and encoders shown generally as 63 and corresponding to the motors 31, 35 and 39 for positioning the scan head and for receiving position data encoded by the encoders, thus enabling the computer 52 to determine and control the positioning of the diagnostic window and the biopsy tool. An ultrasound beam former 64 is coupled to the scanning device 30 and receives data from the scan head thereof for producing 2-D images that are fed to the computer 52 for further processing and 3-D image construction. The computer 52 is controlled via a user interface 66 that typically includes a keyboard and mouse.

Motion and Data Acquisition

The computer, the motors and the high-precision encoders form a closed loop servo-control providing 360° motion allowing stable and backlash-free motion. The computer functions as a tool steering unit for stepwise incremental movement of the motors with an angular resolution that is small enough per step to support high resolution scanning. Full rotation in high resolution mode can take a couple of minutes.

During each incremental stepped rotation of the scan head, the ultrasound system scans a full frame in B mode or Color Angio Mode. A typical probe frequency is between 5-12 MHz. The scan range is adapted to cover the whole breast region, and steering mode may be used if required. Successive 2-D images are sent by the beam former 64 to the computer 52 via an analog or digital video connection. The computer associated the angular position with each image and stores the images in an array images queue for further processing.

Data Processing

The computer includes software that converts the received images to 3-D voxel by voxel by summation of the respective received image pixel taking into account the geometry parameters for the transformation, (cone angle, position angle, steering angle, probe offset and width). The summation operation creates a good signal-to-noise ratio for each voxel, thus yielding a high resolution image having high signal-to-noise ratio.

Other transformations may be performed such as tomography by using Radon transform and back projection techniques.

Data Display

The converted images are represented in orthogonal MPR mode with Coronal, Axial and Sagittal views which enable the operator a quick scrolling for lesion detection. Texture mapping may also be used and a 3-D cube may be displayed to enable the operator to interactively rotate, move and resize the 3-D images. The images display the gray level B scan ultrasound images with Color Doppler Angio overlay and other modality color mapping fused to the ultrasound images.

Other visualization techniques may also be used such as 3-D volume rendering with transparency and light source, MIP-Maximum Intensity projection, Curved MPR, and inversed faded MIP.

As shown in FIG. 8, during the initial scan mode of operation, acoustic gel is applied to the breast, which is then placed within the housing 10 and secured therein by applying suction. The acoustic gel improves acoustic coupling when using an ultra-sound scan head and is not required for other types of radiation, such as γ-rays used in PET and SPECT tomography. Since, during the scan mode, there is no requirement to insert a biopsy tool into the breast, the housing 10 that is used for the scan mode does not require the window defined by the region 18 and can instead be provided with an outer wall having a uniform conical or polyhedral surface. Once the breast is secured within the housing, the second motor 35 and the third (linear) motor 38 are simultaneously operated under control of the computer 52 so as to produce helical scanning of the scan head assembly 39. The circular component of such scanning is unlimited since the scan head 39 assembly is configured for unrestricted rotation around the housing 10. At the end of a complete scan cycle, the scan data are stored in the memory and analyzed in known manner, typically off-line i.e. with the patient absent. The data analysis is text-book knowledge and is described, for example, in "*Digital Picture Processing*" by Azriel Rozenfeld and K. C. Avinash published 1976 by New York: Academic Press.

Figure 9:
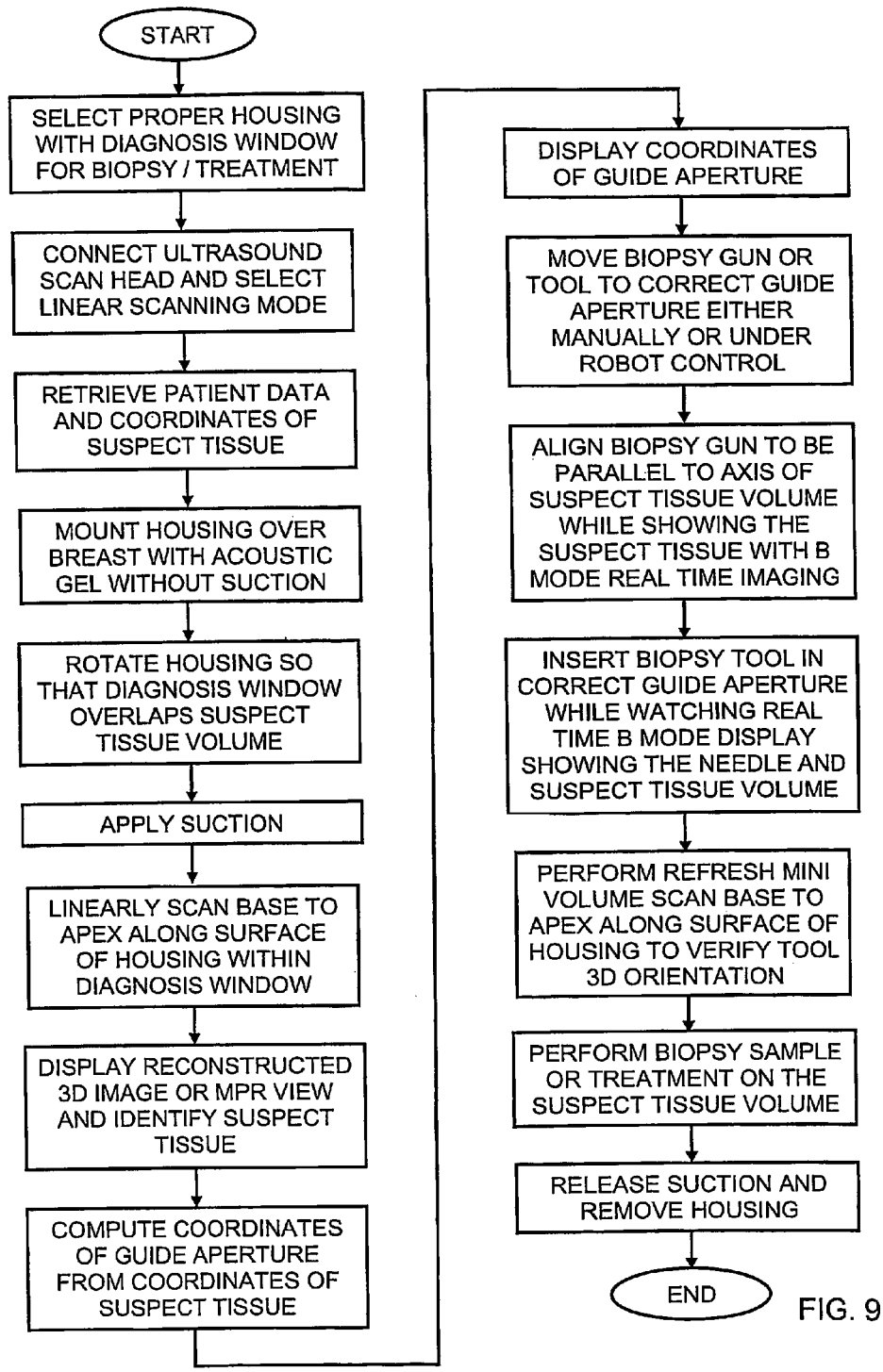

If the analyzed data gives cause for concern that one or more volumes of breast tissue may be tumorous (thus constituting a "suspect tissue volume" or more simply "suspect volume"), the patient must be recalled for a biopsy. As shown in FIG. 6 and will now be described with reference to FIG. 9, the device 30 is located on each of the patient's breasts having a suspected tumor. Seeing that the device 30 is now being used for diagnosis, a biopsy tool must be inserted and, in this case, the housing 10 must be provided with a diagnosis window as defined by the region 18 as shown in FIG. 1*b* for allowing insertion of a biopsy tool 54 through at least one self-sealable aperture thereof. In FIG. 6 the biopsy tool 54 is shown being manipulated into position by a robot shown schematically by a robot arm 55 having at least three degrees of freedom, allowing precise insertion of the biopsy tool 54 through the diagnosis window. Alternatively, as noted above and shown in FIG. 1*b,* the diagnosis window may include a matrix of self-sealable apertures 19 allowing manual insertion of the biopsy tool 54 through a specific aperture that is determined as the closest path to the center of the suspect volume and ensures proper alignment with the volume of suspect tissue as computed by the computer 52. In this case, the aperture coordinates may be identified according to the row and column of the aperture aligned with the suspect volume as computed by the computer 52 and displayed on a display monitor 56 coupled to the computer or printed on a printer (not shown) or other output device.

Regardless of whether the biopsy tool 54 is inserted manually or automatically, use of the device 30 is as follows. Acoustic gel is applied to the breast, which is then placed within the housing 10. Then, and before applying suction, the housing is rotated under control of the computer 52 until the diagnosis window overlaps the suspect volume as previously determined and stored during a scan cycle, so that the biopsy tool can be inserted through the diagnosis window into the suspect tissue. To this end, the motor 31 may be coupled to an encoder (not shown) for scan angle position sensing in known manner. If the biopsy is done immediately after the scanning and analysis without dislocating the housing 10, and if the housing is equipped with a diagnosis window (which it need not be for scanning only) then the housing 10 is simply rotated until the diagnosis window is aligned such that a specific guide aperture as computed by the computer 52 is in proper alignment with the suspect tissue volume. In order to do this, the vacuum must first be released, and the housing 10 rotated until the diagnosis window overlaps the suspect tissue. Seeing that it is then no longer possible to ensure that the housing 10 is positioned relative to the breast in exactly the same registration as was done during the previous scanning session, it is now necessary to calibrate the device and re-determine the precise location of the suspect tissue volume. Such calibration is performed by rotating the housing 10 until the diagnosis window is in approximately the correct location so as to overlap the suspect tissue volume. The breast is then secured in the housing by applying suction. The scan head is then rotated through 90° about the axis C (shown in FIG. 2) so as to be adapted for linear scanning in the direction of B-B along the surface of the housing between opposite ends thereof i.e. from the base to the apex (or vice versa) as shown in FIG. 4. During such linear scanning (referred to as a "mini-volume scan" in FIG. 9) the scan head assembly is not rotated about axis A, so that only the volume of tissue within the diagnosis window is imaged. A 3D image or MPR (multi-planar representation) view is reconstructed and displayed from which suspect tissue is identified using known algorithms. MPR allows the construction of transverse (axial), coronal, or sagittal images. Suitable algorithms for 3-D volume rendering imaging are described in an article entitled "*Volume Rendering*" appearing in "*Computer Graphics*", vol. 22, 1988 by R. A. Drebin and L. Carpenter.

However, as noted above, more commonly the biopsy is performed during a separate session. In any case, the same technique as described above is used to align the diagnosis window by first rotating the housing so that the diagnosis window overlaps the suspect tissue followed by a mini-volume scan so as to calibrate the device and re-determine the precise location of the suspect tissue volume.

If the biopsy tool is to be inserted manually, then the computer 52 computes the location of the suspect tissue from the mini-volume scan, which it then uses to compute the coordinates of a specific guide aperture that is in proper alignment with the suspect tissue volume. The coordinates of the guide aperture are then displayed or otherwise indicated to the clinician or technician, who inserts the biopsy tool 54 through the guide aperture so as to extract the suspect volume of tissue, which is then withdrawn for subsequent analysis. The guide aperture ensures proper alignment of the biopsy tool 54 with the entry coordinates of the suspect tissue volume; but it cannot ensure that the biopsy tool 54 will be correctly oriented in 3-D space for intersecting the suspect tissue volume. To this end, when the biopsy tool 54 is inserted manually, an image of the suspect tissue volume is displayed in real time as a 2-D grayscale ultrasound image at a video refresh rate of 30 frames/sec using B mode real time imaging so as to aid the clinician or technician in inserting the biopsy tool 54 in proper 3-D alignment into the suspect tissue volume. This is done by moving the scan head so that it is aligned with the computed location of the suspect tissue whereby the suspect tissue and the scan head are in a common plane. The plane containing the suspect tissue is imaged during insertion of the biopsy tool through the diagnostic window so as to image the biopsy tool as it moves relative to the suspect tissue. With the scan head position selected for linear scanning, repeated linear scanning along an outer surface of the housing from base to apex is performed so as to obtain successive slices containing the biopsy tool, and a three-dimensional image is constructed showing the tool relative to the suspect tissue.

In the alternative case where the biopsy tool 54 is inserted by a robot 55, an origin of the robot 55 relative to an origin of the diagnosis window is known to the computer by virtue of the pre-calibration described above, thus allowing the robot 55 to be accurately maneuvered by the computer 52 until the biopsy tool 54 is in exact 3-D alignment with the suspect volume of tissue.

Once the biopsy tool 54 is in situ, another "mini-volume" linear scan is performed within the boundary of the diagnosis window from base to apex along surface of housing to verify tool 3-D orientation. This serves to refresh the linear scan which is done when the biopsy tool is inside to make absolutely sure that the tool is right on target and not bent, immediately prior to firing the biopsy tool for sampling the tissue sample. A biopsy sample may now be performed on the suspect tissue volume. Alternatively, the scan head assembly may include a therapeutic head (not shown) locatable in 3-dimensional space for directing radiation through the suspected tissue. The therapeutic head may be a high energy therapeutic ultrasound device or an RF energy ablation device or a cryosurgery device or a Brachytherapy device.

Although in the above-described embodiment, the scan head assembly 39 employs an ultrasound probe 40, according to a different embodiment the scan head is assembly can be adapted to emit high energy particle radiation such as γ-rays.

Figure 10:
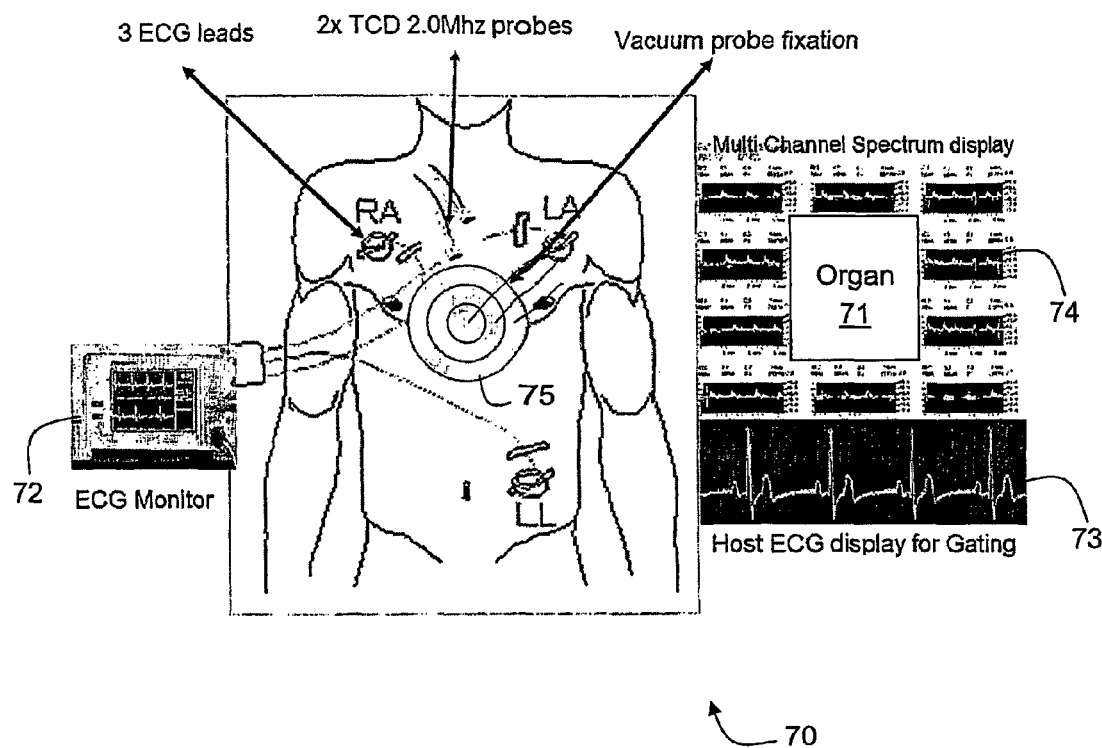
FIG. 10 is a pictorial representation showing a system according to the invention for computing and displaying tissue movement or blood flow.

FIG. 10 is a pictorial representation showing a system 70 according to the invention for computing and displaying tissue movement or blood flow of an organ depicted generally as 71. The standard LA, RA and LL leads of a 3 lead ECG Monitor 72 having an analog or digital output are attached to a patient for monitoring the patient's heart on a display 73 and determining the quiet cardiac phase. A multi-channel and multi-gate Trans-Cranial Doppler (TCD) system depicted as 74 is used for flow detection according to the method described below with reference to FIG. 11 of the drawings. A custom scan head 75 which holds two or more TCD probes with fixed known angles is mounted on the patient's organ 71 after applying an acoustic gel to ensure good acoustic coupling to the skin and the probes are moved around the patient's organ. The TCD system 74 acquires Doppler signals from each location for at least two cardiac cycles and is locked for movement for the acquisition period. The positions of the TCD probes are registered and stored with the Doppler signals as well as the digital waveform of the ECG.

When used for breast scanning, the scan head 75 is adapted for rotary and linear motion relative to a housing mounted on the organ as described above with reference to FIGS. 1a and 1b. The Doppler detectors are mounted for linear motion on a support arm and rotate around a center column so as to perform a complete helical scan of the organ. A step and shoot scanning mode is employed, whereby for each location the probes scan for a few transmit receive cycles which should take at least two cardiac cycles (2-4 sec.). I and Q (in-phase/quadrature-phase) raw data from the received signal are stored in a computer memory (not shown) together with the exact location of the probes and the sampled ECG signal during the acquisition time. The probes are then incremented to the next location and the whole process is repeated. During the acquisition process the computer displays the full spectrum representation for each gate and channel in real time. The Doppler processing includes wall motion filtering, spectrum analysis, and mean/max. frequency shift detection. Gating with the stored ECG wave is required in order to detect diastolic flow. The peak of the ECG "R" waves is detected automatically together with the quiet phase for gating.

Figure 11:
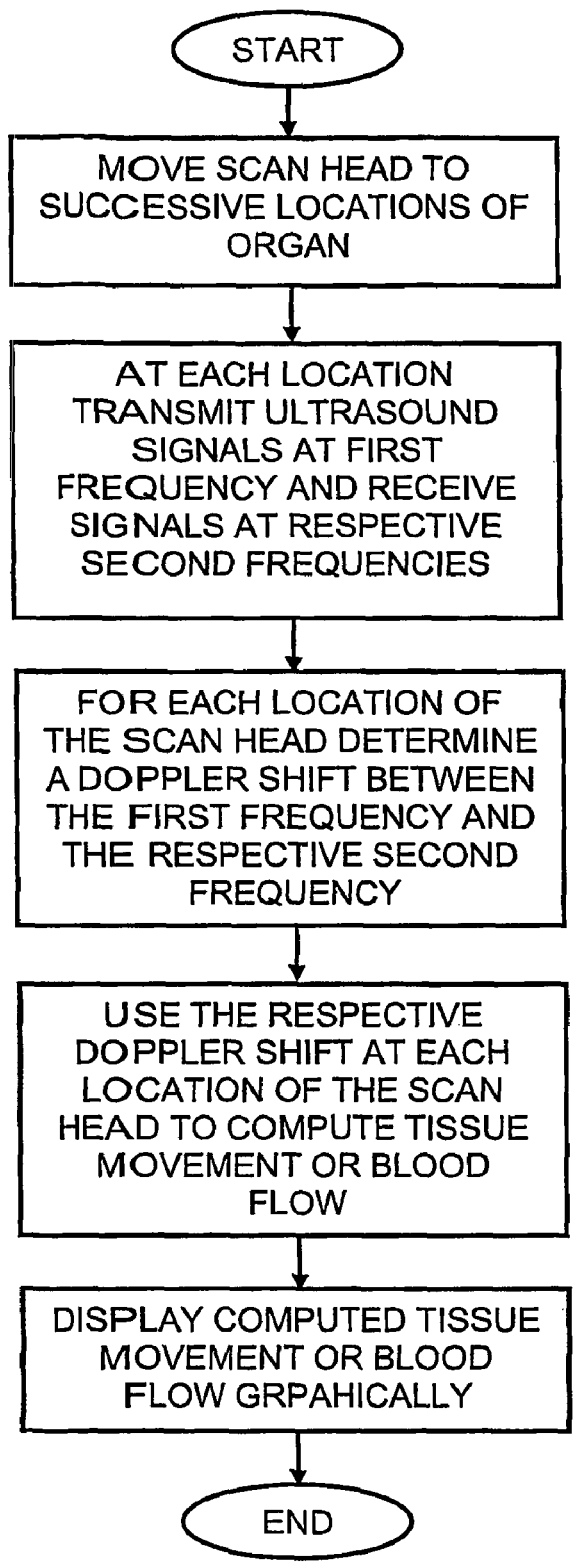
FIG. 11 is a flow diagram showing the principal steps carried out during use of the system shown in FIG. 9.

FIG. 11 is a flow diagram showing the principal steps carried out when using the system 70 for computing and displaying tissue movement or blood flow. The scan head 75 is moved around the patient's organ while emitting ultrasound at a first frequency. At a receiver of the scan head successive ultrasound signals are received each having respective second frequencies. For each location of the scan head 75, mean or maximum Doppler shift between the first frequency and the respective second frequency is determined; and used in known manner to compute tissue movement or blood flow. The computed tissue movement or blood flow is displayed on a display of the TCD system 74, for example as a contour map depicting the tissue movement or blood flow graphically.

Figure 12:
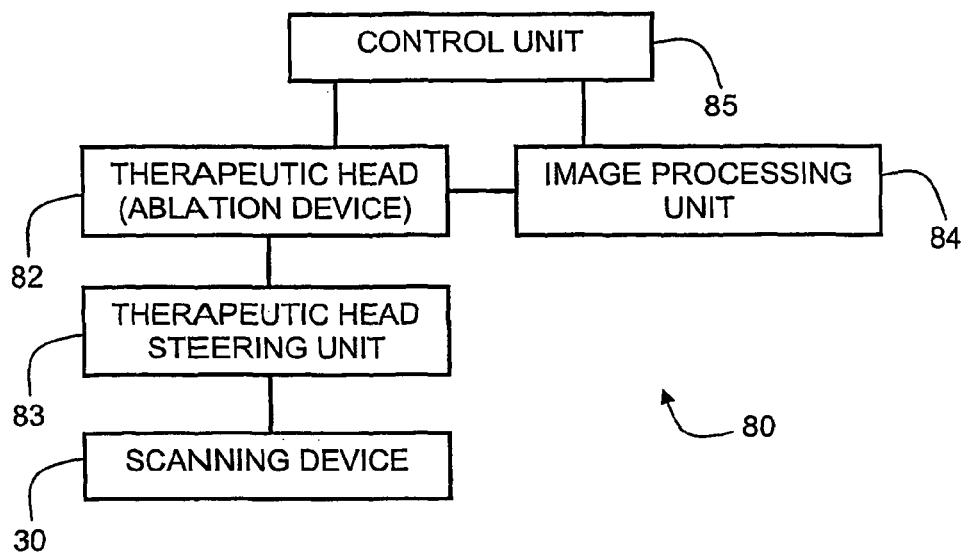
FIG. 12 is a block diagram showing functionally a system for treating suspect tissue according to an exemplary embodiment of the invention.

FIG. 12 is a block diagram showing functionally a system 80 for treating suspect tissue according to an exemplary embodiment of the invention. The system 80 includes the scanning device 30 as shown in FIG. 2 and an ablation device 82 in the form of a high energy ultrasound or RF energy therapeutic head. A steering unit 83 is attached to the ablation device 82 and is independent of the drive unit of scanning device 8430, for moving the ablation device in three degrees of freedom independent of the scan head of the scanning device 8430. An image processing unit 84 is coupled to the ablation device 82 for receiving successive real time two-dimensional images of the tissue being ablated and for analyzing these images for determining an instantaneous temperature of tissue bombarded by RF energy or by high energy ultrasound. A control unit 85 is coupled to the image processing unit 84 and to the ablation device 82 for halting operation thereof when the temperature of tissue reaches a predetermined level. The image processing unit 84 is responsive to a contrast level of bubbles formed by the ablation device 82 for determining the instantaneous temperature of tissue bombarded by RF or Ultrasound energy.

Figure 13:
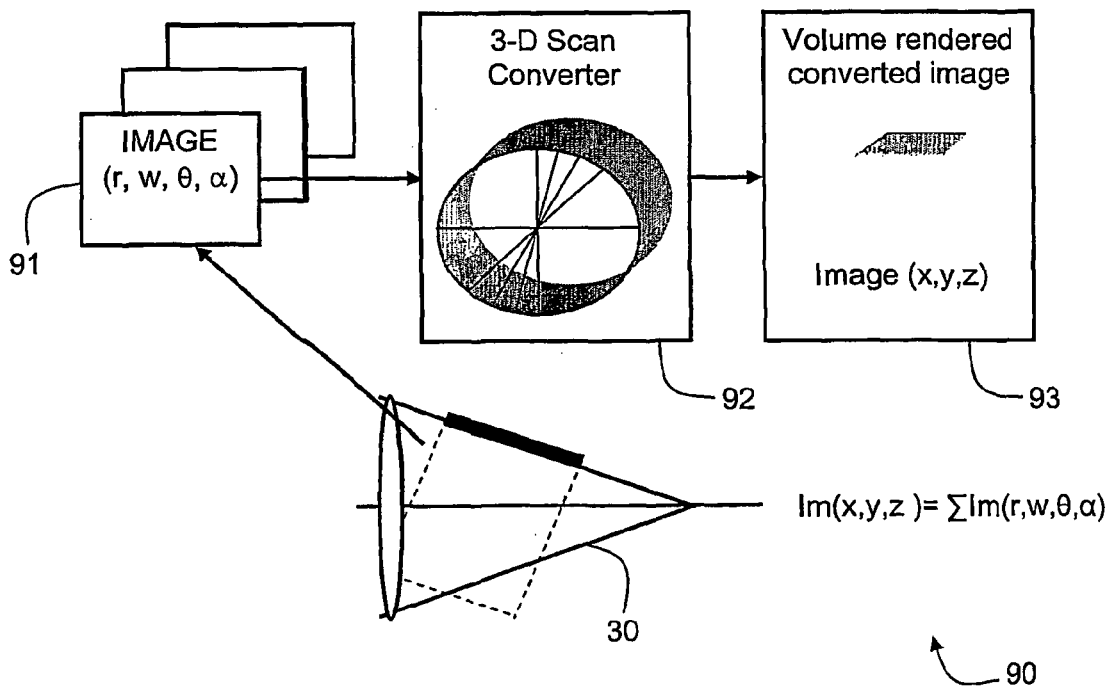
FIG. 13 is a pictorial representation showing the principal stages carried out by an algorithm for computing coordinates of a suspect tissue volume.

FIG. 13 is a pictorial representation showing the principal stages carried out by an algorithm for computing coordinates of a suspect tissue volume scanned using the scanning device 30. Thus, successive 2-D images 91 produced by the scanning device 30 are processed by a 3-D scan converter 92 to construct a 3-D image 93. Brief details of the operation of the 3-D scan converter 92 are now described.

Main Geometrical Model: Scan and Data Accumulation

The first goal in the development of a suitable algorithm for the 3-D scan converter 92 is to create a simple model of the scan and data accumulation processes on the assumption that there are no noise and measurements errors.

Scan

The measured function F (x, y, z) is defined on some volume of interest, which in an actual implementation was the function of ultrasound density. The ultrasound system is used to obtain the sampling of the function F on some volumetric grid, which allows a sequence of planar images $\{f(u, v)\}$ to be obtained, each of which represents the sampling of the measured function F on the plane (u, v), crossing the volume of interest. The geometry $\{G\}$ of every plane is defined by the spatial position of the ultra-sound probe at the moment that the image was obtained, and the parameters of the scan $\{P\}$, i.e. frequency. Thus, the scan process can be represented by the following geometrical transform:

$$F(x, y, z) \xrightarrow{G, P} \{f(u, v)\}$$

Data Accumulation

The reverse problem is the following: starting from the sequence of images $\{f(u, v)\}$, together with their geometrical parameters, reconstruct the volumetric function F (x, y, z).

This problem consists of two separate tasks: geometrical transformation and data accumulation. Geometrically the problem is the reverse to the scan model: knowing the sampling of the volumetric function on the general plane, resample it to the volume. The model of data accumulation deals with the following problem: how to consider together the multiple results of the sampling of the same voxel, coming from different plane samplings. The model should include the confidence parameter.

Support of Different Scanner Geometries

The general form of plane definition as used in the above described geometrical transformation must be fitted to the actual scanner geometry. This may include support for a right cylindrical scanner and a conical scanner. For the conical scanner, axial and helical scan modes are supported.

It will be understood that while the invention has been described with particular reference to ultrasound scanning, diagnosis and treatment of breast tissue, the principles are also applicable to the scanning, diagnosis and treatment of other organs using ultrasound or other forms of energy as are known per se.

When the system is used for biopsy and treatment of other organs such as kidney or liver, the inner and outer cone angle of the housing may be expanded to be near 180° thus permitting use of the same mechanism for the abdomen or chest and allowing the skin surface in the desired scan region to be secured in the housing using suction. In this case the diagnosis can be based on imaging from another modality such as CT/MR, and the ultrasound image can be registered to the CT/MR image using magnetic or optical localization and tracking devices. The operator marks the target volume for biopsy on the CT/MR image. The circular scan head then rotates to a proper position where the real time ultrasound displays the biopsy tool in real time and the robot arm is locked and guides the biopsy tool to the target volume through the computed guide aperture.

It will also be understood that the system according to the invention may include a suitably programmed computer. Likewise, the invention contemplates a computer program being readable by a computer for executing the method of the invention. The invention further contemplates a machine-readable memory tangibly embodying a program of instructions executable by the machine for executing the method of the invention.

The invention claimed is:

1. A portable mechanical high-precision device for performing circular or helical scanning of a patient's organ for tissue diagnosis and/or treatment, comprising:
   a substantially hollow housing having an opening at a first end thereof for accommodating therein said organ or body surface proximate to said organ,
   a securing unit for securing the housing to the organ or body surface during scanning thereof so that the organ or body surface is substantially fixed relative to the housing,
   at least one scan head adapted to scan said organ through said housing, and
   at least one drive unit attached to the housing and to the at least one scan head for allowing unlimited rotation of the scan head relative to the housing.

2. The device according to claim 1, wherein a region of a surface of the housing is provided with at least one aperture to enable penetration of a diagnosis or treatment tool therethrough, said region area having a length substantially equal to an axial length of the housing or a projection of said axial length on said surface.

3. The device according to claim 2, wherein said region has a wall thickness of sufficient dimension to serve as a guide for said tool.

4. The device according to claim 3, wherein said region is a sector of the housing and has a wall thickness that is greater than a wall thickness of a remainder of the housing.

5. The device according to claim 2, wherein the at least one aperture is lined with an elastomeric material that allows penetration of the tool and self-seals when the tool is withdrawn.

6. The device according to claim 2, wherein the at least one aperture is covered with a removable, sealed layer that may be peeled off after applying suction to the housing.

7. The device according to claim 1, wherein the housing is disposable.

8. The device according to claim 1, wherein the housing includes:
   an inner portion for securing on to a surface of the patient's body, and
   an outer portion coupled to the drive unit and adapted for movement relative to the inner portion together with the scan head.

9. The device according to claim 8, wherein:
   a region of a surface of the inner portion is provided with at least one self-sealable aperture to enable penetration of a diagnosis or treatment tool therethrough, said region having a length substantially equal to an axial length of the housing or a projection of said axial length on said surface; and
   the outer portion is provided with a window that allows penetration of said tool through the inner portion when the window overlaps said region.

10. The device according to claim 9, wherein said area has a wall thickness of sufficient dimension to serve as a guide for the tool.

11. The device according to claim 10, wherein said area is a sector of the housing and has a wall thickness that is greater than a wall thickness of a remainder of the housing.

12. The device according to claim 9, wherein the self-sealable holes are lined with an elastomeric material that allows penetration of the biopsy tool and self-seals when the biopsy tool is withdrawn.

13. The device according to claim 9, wherein the self-sealable holes are covered with a removable, sealed layer that may be peeled off after applying suction to the housing.

14. The device according to claim 8, wherein the inner portion is disposable.

15. The device according to claim 1, wherein the securing unit is adapted to apply vacuum pressure.

16. The device according to claim 1, wherein the housing is shaped for accommodating a woman's breast.

17. The device according to claim 16, wherein an inside end of the housing is solid.

18. The device according to claim 1, wherein the drive unit includes a motor coupled to an encoder for scan angle position sensing.

19. The device according to claim 1, wherein a wall of the housing includes at least one planar section.

20. The device according to claim 19, wherein a surface of the housing is polyhedral.

21. The device according to claim 1, wherein the at least one scan head emits high energy particle radiation.

22. The device according to claim 1, wherein the at least one scan head emits ultrasound energy.

23. The device according to claim 1, wherein the at least one scan head is configured for selection between a first position wherein the scan head is adapted for rotary scanning around a surface of the housing and a second position wherein the scan head is adapted for linear scanning along the surface of the housing between opposite ends thereof.

24. A method for using the device according to claim 23, the method including:
- moving the scan head relative to the patient's organ while emitting ultrasound at a first frequency;
- receiving at a receiver of the scan head successive ultrasound signals each having respective second frequencies;
- for each location of the scan head determining a Doppler shift between the first frequency and the respective second frequency;
- using the respective Doppler shift at each location of the scan head to compute tissue movement or blood flow; and
- displaying data representative of the computed tissue movement or blood flow.

25. The method according to claim 23, wherein said data is a contour map depicting said tissue movement or blood flow graphically.

26. The method according to claim 24, wherein areas having equal tissue movements are depicted by areas having an identical display characteristic.

27. A system for treating suspect tissue, said system comprising:
- a device according to claim 1, and
- a tool locatable in 3-dimensional space for introducing into the suspected tissue.

28. The system according to claim 26, including a tool steering unit attached to the tool and being independent of the drive unit, for moving the tool in 3 degrees of freedom independent of the scan head.

29. A system for treating suspect tissue, said system comprising:
- a device according to claim 1, and
- a therapeutic head locatable in 3-dimensional space for directing radiation through the suspected tissue.

30. The system according to claim 28, including a therapeutic head steering unit attached to the therapeutic head and being independent of a drive unit of said device, for moving the therapeutic head in three degrees of freedom independent of the scan head.

31. The system according to claim 29, wherein the therapeutic head is a high energy therapeutic ultrasound device.

32. The system according to claim 29, wherein the therapeutic head is an RF energy ablation device.

33. The system according to claim 29, wherein the therapeutic head is a cryosurgery device.

34. The system according to claim 29, wherein the therapeutic head is a Brachytherapy device.

35. The system according to claim 29, further including:
- an image processing unit for receiving successive real time two-dimensional images of the tissue being ablated and for analyzing said images for determining an instantaneous temperature of tissue bombarded by RF energy or by high energy ultrasound, and
- a control unit coupled to the image processing unit and to the RF energy or high energy ultrasound ablation device for halting operation of the RF energy or high energy ultrasound ablation device when the temperature of said tissue reaches a predetermined level.

36. The system according to claim 35, wherein the image processing unit is responsive to a contrast level of bubbles formed by the ablation device for determining the instantaneous temperature of tissue bombarded by RF or Ultrasound energy.

37. A method for performing diagnosis of a suspect tissue volume using a biopsy tool, said method comprising:
- determining an initial location of the suspect tissue volume relative to the scan head of a device according to claim 1;
- affixing said device so that a diagnosis window of the device overlaps said initial location;
- partially scanning the patient's organ so as to identify at least a portion of the suspect tissue volume and determine coordinates thereof;
- computing a location and 3-D orientation within the diagnosis window for correctly inserting the biopsy tool; and
- orienting the biopsy tool in said 3-D orientation and inserting into the suspect tissue volume through said location of the diagnosis window.

38. The method according to claim 37, for use with a device having a matrix of apertures over the diagnosis window, each of said apertures having a known identifiable coordinate relative to an origin of the diagnosis window, the method including:
- displaying an image of the suspect tissue volume;
- computing coordinates of a guide hole aligned with the suspect tissue volume; and
- identifying said guide hole to a clinician or technician for inserting the biopsy tool through said guide hole in proper 3-D orientation.

39. The method according to claim 37, wherein affixing said device so that said area overlaps said initial location includes:
- mounting the housing over a surface of the patient's body;
- moving the housing until said area overlaps the initial location; and
- securing the housing relative to said surface of the patient's body.

40. The method according to claim 37, wherein partially scanning includes linearly scanning along an outer surface of the housing within said diagnostic window.

41. The method according to claim 37, including:
- returning the scan head so that it is aligned with the computed location of the suspect tissue whereby the suspect tissue and the scan head are in a common plane; and
- imaging the plane containing the suspect tissue while inserting the biopsy tool through said diagnostic window so as to image the biopsy tool as it moves relative to the suspect tissue.

42. The method according to claim 39, further including:
- repeatedly linearly scanning along an outer surface of the housing so as to obtain successive slices containing the biopsy tool; and
- constructing a three-dimensional image showing the tool relative to the suspect tissue.

43. The method according to claim 37, further including therapeutically treating the suspect tissue.

44. A computer program comprising computer program code for performing the method of claim 24 when said program is run on a computer.

45. The device according to claim 1 wherein the housing is shaped for molding a woman's breast.

* * * * *